(12) United States Patent
Khuon et al.

(10) Patent No.: US 9,179,866 B2
(45) Date of Patent: *Nov. 10, 2015

(54) SELF-CONTAINED CARDIAC RESPONSE UNIT

(71) Applicant: ZOLL Medical Corporation, Chelmsford, MA (US)

(72) Inventors: Pisit Khuon, Johnston, RI (US); Mark Totman, Winchester, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/330,392

(22) Filed: Jul. 14, 2014

(65) Prior Publication Data

US 2014/0323923 A1 Oct. 30, 2014

Related U.S. Application Data

(63) Continuation of application No. 13/784,197, filed on Mar. 4, 2013, now Pat. No. 8,798,743.

(51) Int. Cl.
*A61N 1/04* (2006.01)
*A61B 5/113* (2006.01)
*A61N 1/39* (2006.01)

(52) U.S. Cl.
CPC .............. *A61B 5/113* (2013.01); *A61N 1/0492* (2013.01); *A61N 1/3968* (2013.01)

(58) Field of Classification Search
None
See application file for complete search history.

(56) References Cited

U.S. PATENT DOCUMENTS

| | | | |
|---|---|---|---|
| 5,154,335 A | 10/1992 | Bredow et al. | |
| 5,496,257 A | 3/1996 | Kelly | |
| 5,797,969 A | 8/1998 | Olson et al. | |
| 6,115,638 A | 9/2000 | Groenke et al. | |
| 6,125,299 A | 9/2000 | Groenke et al. | |
| 6,306,107 B1 | 10/2001 | Myklebust et al. | |
| 6,390,996 B1 | 5/2002 | Halperin et al. | |
| 6,599,258 B1 | 7/2003 | Bystrom et al. | |
| 6,694,193 B2 * | 2/2004 | Jonsen et al. | 607/142 |
| 7,016,727 B2 | 3/2006 | Powers et al. | |
| 7,220,235 B2 | 5/2007 | Geheb et al. | |
| 7,245,974 B2 | 7/2007 | Dupelle et al. | |
| 7,706,878 B2 | 4/2010 | Freeman | |
| 7,801,605 B2 | 9/2010 | Smirles et al. | |
| 8,010,190 B2 | 8/2011 | Olson et al. | |
| 8,010,192 B2 | 8/2011 | Zhu et al. | |
| 8,014,859 B2 | 9/2011 | Vaisnys et al. | |
| 8,096,962 B2 | 1/2012 | Palazzolo et al. | |
| 8,346,375 B2 | 1/2013 | Jonsen et al. | |
| D675,739 S | 2/2013 | McCormack | |
| 2001/0047140 A1 | 11/2001 | Freeman | |
| 2008/0140171 A1 * | 6/2008 | Roberts et al. | 607/142 |
| 2010/0234908 A1 | 9/2010 | Didon | |
| 2010/0241181 A1 | 9/2010 | Savage et al. | |
| 2013/0282069 A1 | 10/2013 | Thiagarajan et al. | |

* cited by examiner

*Primary Examiner* — Brian T Gedeon
(74) *Attorney, Agent, or Firm* — Fish & Richardson P.C.

(57) ABSTRACT

An apparatus includes a housing including a first side and a second side; a chest compression sensor coupled with the second side of the housing; at least one compartment partially formed by one of the first side and the second side of the housing; and at least one removable defibrillator electrode pad contained in the at least one compartment partially formed by one of the first side and the second side of the housing.

17 Claims, 5 Drawing Sheets

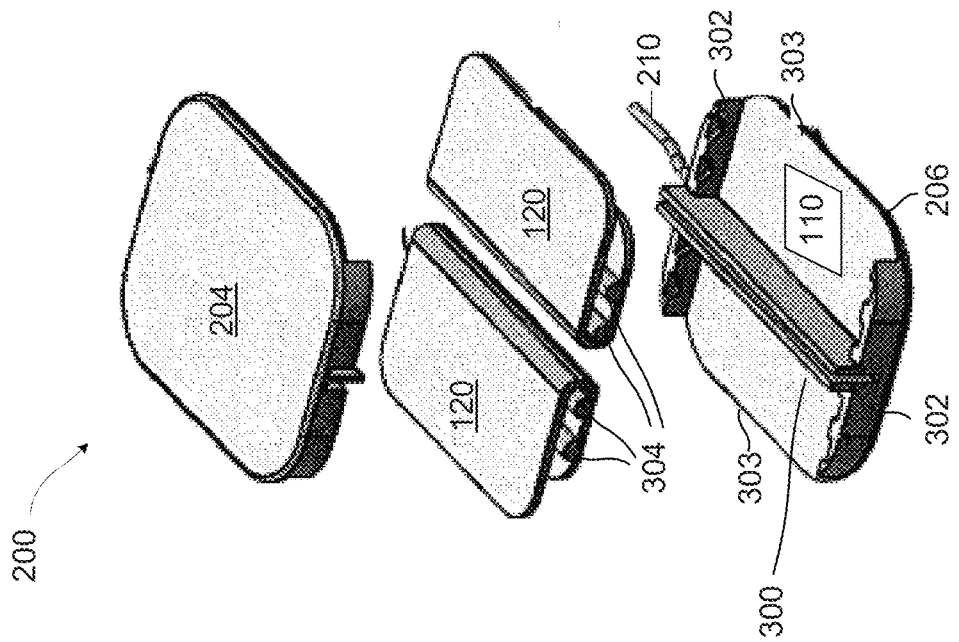
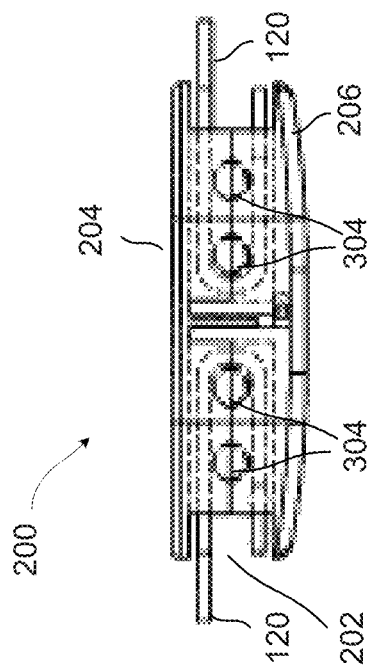
FIG. 3B
FIG. 3A

SELF-CONTAINED CARDIAC RESPONSE UNIT

CLAIM OF PRIORITY

This application is a continuation of and claims priority under 35 U.S.C. §120 to U.S. patent application Ser. No. 13/784,197, filed on Mar. 4, 2013, the entire contents of which are hereby incorporated by reference.

TECHNICAL FIELD

This document relates to a self-contained cardiac response unit, e.g., for use during cardio-pulmonary resuscitation (CPR) treatment.

BACKGROUND

Sudden health problems such as sudden cardiac arrest and injuries caused by accidents kill thousands of people and cause permanent injury every year. Fast and competent care to resuscitate such victims of these problems can be essential to positive outcomes in such situations. For example, it is said that the chance of surviving a sudden cardiac arrest falls by ten percent for every minute of delay in providing effective treatment.

Resuscitation treatments for patients suffering from cardiac arrest generally include clearing and opening the patient's airway, providing rescue breathing for the patient, and applying chest compressions to provide blood flow to the victim's heart, brain, and other vital organs. If the patient has a shockable heart rhythm (ventricular fibrillation or pulseless ventricular tachycardia), resuscitation also may include defibrillation therapy. Along with such action, an electrocardiogram (ECG) signal for the patient may be electronically captured, displayed, and monitored, so that rescuers can determine when the patient's heart has returned to normal or near-normal operation, and determine when the heart exhibits a shockable rhythm.

SUMMARY

A self-contained response unit for use by a caregiver providing resuscitation to a victim of cardiac arrest includes one or more defibrillator electrode pads and one or more sensors contained within a compartment of the response unit. The electrode pads can be removed from the compartment of the response unit and positioned on the chest of the victim such that a defibrillator can provide defibrillation to the victim through the pads. The sensors are integrated into a bottom side of the response unit and sense physical movement, such as the movement of chest compressions being applied to the victim when the caregiver delivers cardiopulmonary resuscitation (CPR) to the victim. The containment of both defibrillator electrode pads and sensors in a single unit helps the caregiver to provide treatment to the victim more efficiently.

In a general aspect, an apparatus includes a housing comprising a first side and a second side; a chest compression sensor coupled with the second side of the housing; at least one compartment partially formed by one of the first side and the second side of the housing; and at least one removable defibrillator electrode pad contained in the at least one compartment partially formed by one of the first side and the second side of the housing.

Embodiments may include one or more of the following.

The apparatus includes a dispenser disposed in the at least one compartment and configured to facilitate removal of the at least one removable defibrillator electrode pad. In some cases, the at least one removable defibrillator electrode pad is arranged on the dispenser. In some cases, the dispenser is a roller. In some cases, the dispenser is coated with a release liner.

At least a portion of the at least one removable defibrillator electrode pad is rolled around a roller disposed between the first side and the second side of the housing. In some cases, the at least one removable defibrillator electrode pad is configured to be unrolled during removal of the removable defibrillator electrode pad from between the first side and the second side of the housing.

The apparatus includes two removable defibrillator electrode pads configured to be placed on a chest of a victim of cardiac arrest, the removable defibrillator electrode pads for use with a defibrillator. In some cases, each removable defibrillator electrode pad is arranged on a corresponding dispenser disposed between the first side and the second side of the housing.

The chest compression sensor includes a motion detection device, such as an accelerometer.

The apparatus includes a cover configured to enclose the at least one removable defibrillator electrode pad within the compartment partially formed by one of the first side and the second side of the housing. In some cases, the cover is at least one of airtight and watertight. In some cases, the cover includes a hermetic seal disposed at least around the sides of the housing. In some cases, the cover is configured to enclose the housing.

The housing is configured to be placed on a chest of a victim of cardiac arrest such that the chest compression sensor can measure parameters associated with chest compressions applied to the victim.

The apparatus includes a cable in electrical communication with the chest compression sensor and configured to be connected to a defibrillator.

The apparatus includes a cable port in electrical communication with the chest compression sensor and configured to receive a cable connected to a defibrillator.

In a general aspect, a method includes providing a housing comprising a first side and a second side. A chest compression sensor is coupled with the second side of the housing. The method includes removing at least one removable defibrillator electrode pad from a compartment partially formed by one of the first side and the second side of the housing.

Embodiments may include one or more of the following.

Removing the at least one removable defibrillator electrode pad includes removing the at least one removable defibrillator electrode pad from a dispenser disposed in the compartment.

Removing the at least one removable defibrillator electrode pad includes removing the at least one removable defibrillator electrode pad from a roller disposed in the compartment. In some cases, removing the at least one removable defibrillator electrode pad includes unrolling the at least one removable defibrillator electrode pad.

The method includes opening a cover enclosing the at least one removable defibrillator electrode pad within the compartment.

The method includes positioning the housing on a chest of a victim of cardiac arrest.

The method includes positioning the at least one removable defibrillator electrode pad on a chest of a cardiac arrest victim.

The method includes removing two removable defibrillator electrode pads from corresponding compartments. In some cases, the method includes positioning the two removable defibrillator electrode pads on a chest of a cardiac arrest victim. In some cases, the method includes electrically connecting each of the two removable defibrillator electrode pads with a component of a defibrillator.

The method includes electrically connecting the chest compression sensor to a defibrillator.

In a general aspect, an apparatus includes a housing comprising a first side and a second side; a chest compression sensor coupled with the second side of the housing; a compartment partially formed by one of the first side and the second side of the housing; at least two rollers disposed in the compartment, the at least two rollers coated with a release liner; and at least two removable defibrillator electrode pads, each removable defibrillator pad arranged on a corresponding one or more of the two rollers.

Embodiments may include one or more of the following.

The at least two removable defibrillator electrode pads are configured to be unrolled during removal of the removable defibrillator electrode pads from between the first side and the second side of the housing.

The chest compression sensor comprises an accelerometer.

The apparatus includes a cover configured to enclose the at least two removable defibrillator electrode pads within the compartment partially formed by one of the first side and the second side of the housing.

The housing is configured to be placed on a chest of a victim of cardiac arrest such that the chest compression sensor can measure parameters associated with chest compressions applied to the victim.

The self-contained response unit described herein may have one or more of the following advantages. Containment of both defibrillator electrode pads and sensors in a single unit helps the caregiver to provide treatment to the victim more efficiently, improving treatment outcomes. Handling of the defibrillator electrode pads by the caregiver is reduced, thus contributing to improved performance of the electrode pads and enabling the caregiver to deploy the electrode pads efficiently. The deployment of the self-contained response unit is straightforward and layered visual cues on the components of the response unit help the caregiver to understand the operation of the response unit.

Other features and advantages are apparent from the following description and from the claims.

BRIEF DESCRIPTION OF DRAWINGS

FIG. 3A is a front view diagram of one embodiment of a self-contained response unit.

FIG. 3B is an exploded view diagram of the embodiment of the self-contained response unit shown in FIG. 3A.

DETAILED DESCRIPTION

A self-contained response unit for use by a caregiver providing resuscitation to a victim of cardiac arrest includes one or more defibrillator electrode pads and one or more sensors contained within a compartment of the response unit. The defibrillator electrode pads can be removed from the compartment of the response unit and positioned on the chest of the victim such that a defibrillator can provide defibrillation to the victim through the pads. The sensors may be integrated into a bottom side of the response unit and sense physical parameters, such as chest compression rate and depth, when the caregiver delivers cardiopulmonary resuscitation (CPR) to the victim. The containment of both defibrillator electrode pads and sensors in a single unit helps the caregiver to provide treatment to the victim more efficiently.

Figure 1:
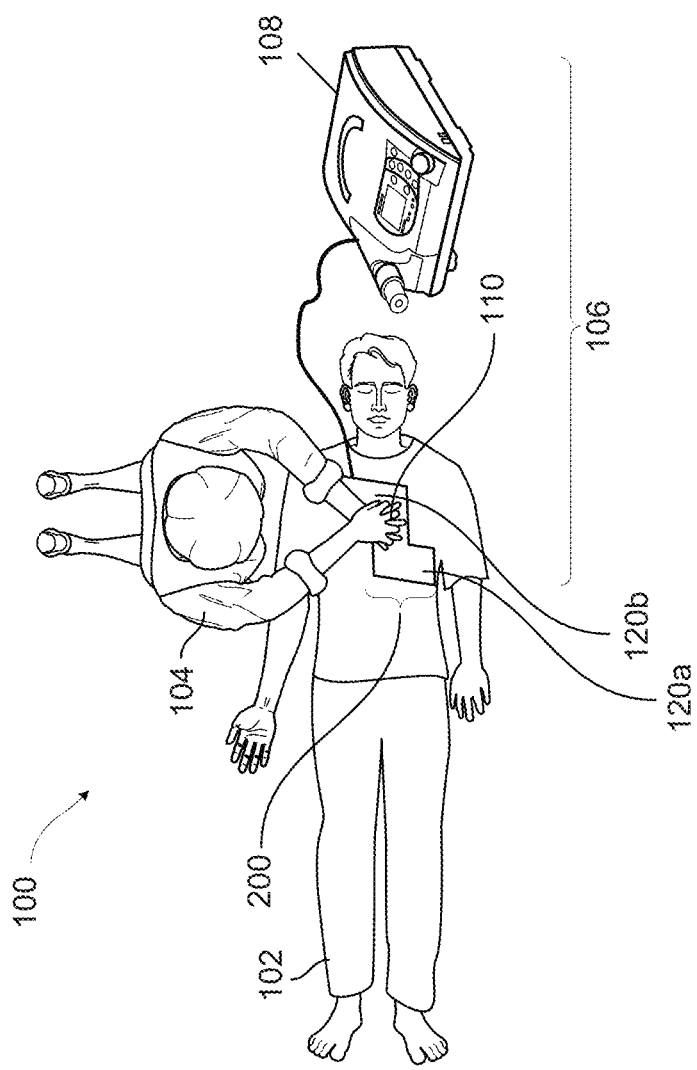
FIG. 1 is a diagram of a rescue scene.

Referring to FIG. 1, at a rescue scene 100, a caregiver 104 performs cardiopulmonary resuscitation (CPR) on a victim 102 or patient 102 (the terms are used interchangeably here to indicate a person who is the subject of intended or actual CPR and related treatment, or other medical treatment), such as an individual who has apparently undergone sudden cardiac arrest. The caregiver may be, for instance, a civilian responder with limited or no training in lifesaving techniques; a first responder, such as an emergency medical technician (EMT), police officer, or firefighter; or a medical professional, such as a physician or nurse. The caregiver 104 may be acting alone or may be acting with assistance from one or more other caregivers, such as a partner EMT.

The caregiver 104 can also deploy defibrillator electrode pads 120a, 120b (also referred to generally as defibrillator electrode pads 120) included in a self-contained response unit 200 for use with an electronic defibrillating system 106 including a defibrillator, such as an automated external defibrillator (AED) 108, a professional defibrillator, or another type of defibrillating apparatus. The AED 108 may take a variety of forms, such as the ZOLL MEDICAL R Series, E Series, or M Series defibrillators. The response unit 200 can also include one or more sensors 110 that move with the victim's chest during application of chest compressions and provide a measure of the vertical displacement of such motion. The defibrillator electrode pads 120 and the sensor 110 may provide signals to the AED 108, based on which the AED 108 can instruct the caregiver 104 in performing CPR. For example, the electrical impedance present in the chest of the patient 102 may be measured between the electrode pads 120 and provided in a signal to the AED 108. Such an impedance signal may be used for a variety of operations of the AED 108, for example, based upon the measured impedance, the AED 108 may adjust the amount of current applied to the victim's heart during defibrillation (e.g., high impedance may call for an increased current level). The impedance across the patient's chest can also be used to detect the airflow activities (e.g., respiration, ventilation, etc.) of the victim. As the patient's lungs expand and contract, the geometry of the patient's chest changes that causes the measured impedance to correspondingly change.

The sensor 110 may collect signals and sense other phenomena. For example, the response unit 200 may include a sensor for collecting electrocardiogram (ECG) signals read from the victim 102. The response unit 200 may also include a sensor measuring chest compressions applied to the patient 102. For example, a sensor may be positioned in a location where the caregiver 104 is to place the palms of their hands when performing CPR chest compressions on the victim 102. As a result, the sensor may move with the victim's chest and the caregiver's hands, and provide a measure of the vertical displacement of such motion.

Figure 2A:
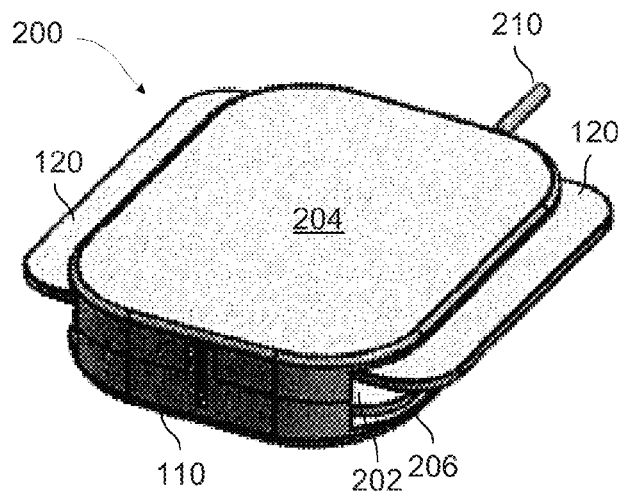
FIGS. 2A and 2B are diagrams of one embodiment of a self-contained response unit prior to and following defibrillator electrode pad deployment, respectively.
Figure 2B:
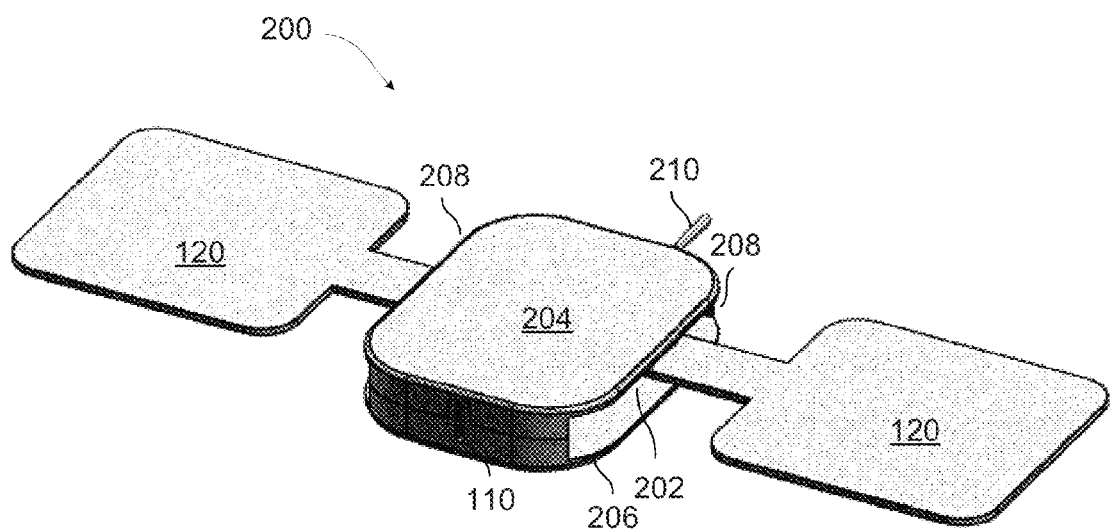

Referring to FIGS. 2A and 2B, a self-contained response unit 200 for use by the caregiver 104 contains defibrillator electrode pads 120, such as multi-function electrode (MFE) pads, and a sensor 110 (or multiple sensors). In one example, the defibrillator electrode pads 120 are disposed in a compartment 202 between a top side 204 and a bottom side 206 of the response unit 200. The sensor 110 can be coupled to the response unit 200, e.g., coupled to the top side 204 or the bottom side 206 (as shown in FIGS. 2A and 2B) of the response unit. For instance, the sensor 110 may be coupled to a circuit board that is attached to the top side 204 or the bottom side 206 of the response unit 200.

During deployment of the response unit 200, the defibrillator electrode pads 120 can be removed and detached from the response unit 200. For instance, the caregiver 104 may grasp the defibrillator electrode pads and pull the defibrillator electrode pads out of the response unit through openings 208 of the response unit 200, e.g., on the sides of the response unit 200. The defibrillator electrode pads can then be positioned on the victim (e.g., on the chest of the victim) for delivery of defibrillation therapy. During delivery of CPR, the response unit 200 itself can be positioned on the chest of the victim, e.g., with the bottom side 206 contacting the center of the victim's chest, such that the sensor 110 or sensors can monitor the delivery of CPR to the victim, the current real-time condition or physical parameters of the victim, and/or other signals. The caregiver can perform CPR by placing his hands on the top side 204 of the response unit 200 and applying compressions to the chest of the victim through the response unit.

The sensor 110 and/or defibrillator electrodes 120 can be connected to an AED or other type of defibrillator or other electronic device (e.g., a computer). In some examples, a cable 210 is electrically connected to the sensor 110 and/or defibrillator electrodes 120 and can be plugged into an AED or other device. In some examples, a port electrically connected to the sensor 110 can receive a cable, such as a cable supplied with an AED or other device, to establish communication with the AED or other device. In some examples, the bottom side 206 of the response unit can include electrical and/or mechanical contacts, such as screws, rivets, USB ports, electrical jacks, or other contacts, for connecting the cable 210 or port to the sensor and/or defibrillator electrodes. In some examples, the response unit 200 includes a communications module that is capable of communicating wirelessly with the AED or another device, such as via a wireless network, a cellular telephone network (e.g., a 3G or 4G network), a Bluetooth connection, or another wireless connection.

The AED 108 may use signals from the sensor 110 and/or the defibrillator electrode pads 120 to attain a measure of ventilations being applied to the patient 102 or other types of airflow activities associated with the patient (e.g., unassisted inhaling and exhaling of the patient, etc.). For example, an impedance signal measured across the chest of the patient 102 may be processed for representing airflow activities (e.g., ventilations, unassisted breathing by the patient, etc.) and to determine if the patient is being over ventilated. For instance, the impedance signal may provided by passing electrical current between two defibrillator electrode pads 120 positioned on the chest of the patient 102, however, other techniques may be employed for measuring electrical impedance across the patient's chest. Also, different types of electrode configurations may be implemented. For example, more than two electrodes may be used in some arrangements for measuring the impedance present in the patient's chest.

A signal representative of chest compressions applied to a patient may also be received and processed by the AED 108. For example, the sensor 110 may include an accelerometer assembly, such as a housing inside which is mounted an accelerometer sensor configuration. The accelerometer assembly may be positioned in a location where the caregiver 104 is to place the palms of their hands when performing CPR chest compressions on the victim 102. As a result, the accelerometer assembly may move with the victim's 102 chest and the caregiver's hands, and acceleration of such movement may be double-integrated to identify a vertical displacement of such motion. In some arrangements the accelerometer assembly may include two or more accelerometers that may be used in concert to provide the chest compression signal (e.g., provide an averaged signal from the multiple sensors) to the AED 108. Further, other types of technology may be employed alone or in combination (e.g., in concert with the accelerometer assembly) to produce a signal representative of chest compressions. For example, one or more pressure sensors, ultrasound technology, string gauges, laser interferometry, magnetic field technology, etc. may implemented for providing chest compression signals. Different types of signals may also be used for attaining information representative of chest compressions.

Provided the impedance signal and the chest compression signal, the AED 108 may implement one or more techniques to process the signals to identify airflow activities of the patient 102 such as occurrences of ventilations, unassisted respiratory activities, etc. For instance, the AED 108 may include a signal processor that processes the provided signals. The signal processor may be software based (e.g., one or more processes, routines, operations, functions, etc.), hardware based (e.g., one or more general processing units, specialized processing units, etc.), software and hardware based, etc. In addition to using the information provided by the signals (e.g., the impedance signal, chest compression signal, etc.), the signal processor may also use information from other sources, for example, locally stored data (e.g., stored in one or more memories in the AED 108), data stored external to the AED (e.g., in one or more remote memories that may or may not be network accessible), etc. By processing the received signals, and potentially using other information, the signal processor may initiate the production of one or signals for alerting the caregiver 104. For example, one or more feedback signals (e.g., an audible alert signal) may be produced and provided to the caregiver 104 for initiating appropriate action (e.g., reduce the frequency of ventilations applied to the patient). Other types of feedback signals may also be initiated by the signal processor. For example, visual signals provided from a series of light emitting diodes (LEDs), one or more graphical displays, etc. may be used for providing feedback (e.g., alerts, instructions, etc.) to the caregiver 104.

FIGS. 3A and 3B show one example of the self-contained response unit 200. The defibrillator electrode pads 120 are contained in the compartment 202 between the top side 204 and the bottom side 206 of the response unit 200. In some examples, the compartment is open on its four lateral sides. In some examples, a cover that may include a rigid wall or a flexible seal, encloses one or more sides of the compartment 202. For instance, in the example of FIGS. 3A and 3B, walls 302 are present on two sides of the compartment 202, and openings 303 are present on the remaining two sides. A support beam 300 in the compartment 202 provides mechanical strength to the response unit 200, e.g., to prevent the compartment 202 from collapsing against the compressive force that the response unit receives during application of chest compressions and to transfer the force from the top side 204 to the bottom side 206 of the response unit 200.

One or more dispensers, such as rollers 304, are contained in the compartment 202. One or more defibrillator electrode pads 120 can be arranged on a corresponding one or more dispensers 304. For instance, in the example of FIGS. 3A and 3B, each defibrillator electrode pad 120 is rolled around two rollers 304 fixed to the walls 302 of the compartment 202. To remove a defibrillator electrode pad 120, a caregiver can pull the defibrillator electrode pad 120 out of one of the openings 303 of the compartment 202, causing the defibrillator electrode pad 120 to roll off of the roller 304. In some examples, the defibrillator electrode pads 120 are stored in a flat or folded configuration in the compartment 202. In some examples, the defibrillator electrode pads 120 are rolled on themselves rather than on rollers and can be removed from the compartment 202 and then unrolled.

In some examples, the dispensers 304 can be coated with a release liner, such as silicone, to enable the defibrillator electrode pads 120 to be removed quickly and easily and with little or no damage. In some examples, the defibrillator electrode pads 120 can have no release liner coating and thus can be immediately placed on the victim upon removal from the response unit 200, enabling the caregiver to quickly and efficiently provide care to the victim. In some examples, the defibrillator electrode pads 120 can have a release liner coating, which can be removed by the caregiver after removing the defibrillator electrode pads 120 from the response unit 200 and prior to placing the defibrillator electrode pads 120 on the victim.

In some examples, a bottom face of the bottom side 206 of the response unit 200 can be coated with an adhesive that causes the response unit 200 to adhere to the victim's chest. The adhesive can be coated with a release liner that can be removed by the caregiver prior to placing the response unit 200 on the victim's chest. In some examples, the response unit 200 can be positioned on the victim's chest with no adhesive.

The response unit 200 can be sized such that the caregiver can easily apply chest compressions to the victim with his hands positioned on the top side 202 of the response unit 200. For instance, the length and width of the response unit can be approximately the size of an adult hand (e.g., about 3 to 6 inches in length and width). The height of the response unit 200 can be small enough that the caregiver's hands can be close to the victim's chest when applying chest compressions to the victim. For instance, the height of the response unit 200 can less than about one inch.

In some examples, the response unit 200 and/or the sensor 110 can be provided at least partially enclosed in packaging, e.g., to protect the integrity and cleanliness of the electrode pads 120 and/or the sensor 110. For instance, the response unit 200 can be packaged in a cover that provides a high moisture vapor barrier, such as a container including a gasket that engages with the openings 303 of the compartment 202. The response unit 200 can also be packaged in a high moisture vapor transmission rate (MVTR) material, such as a polyfoil substrate that is hermetically sealed to the open sides 303. The response unit 200 can also be enclosed in its entirety in a cover.

Figure 4:
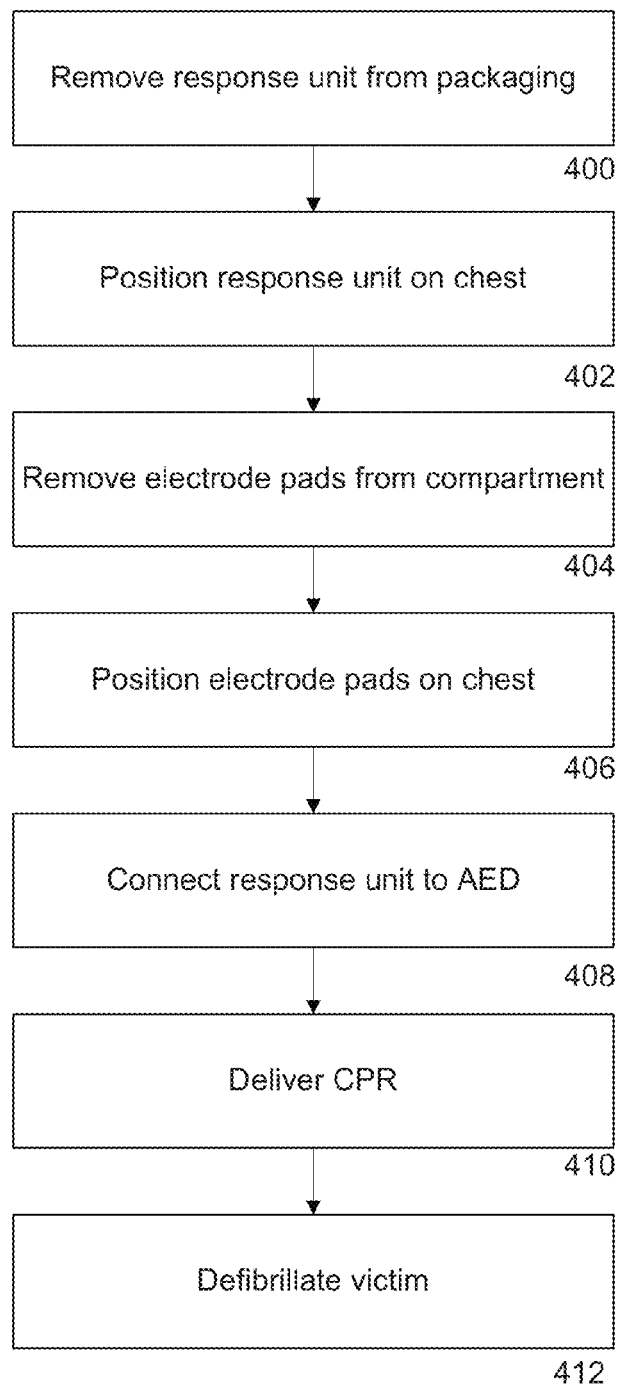
FIG. 4 is a flowchart.
Figure 5:
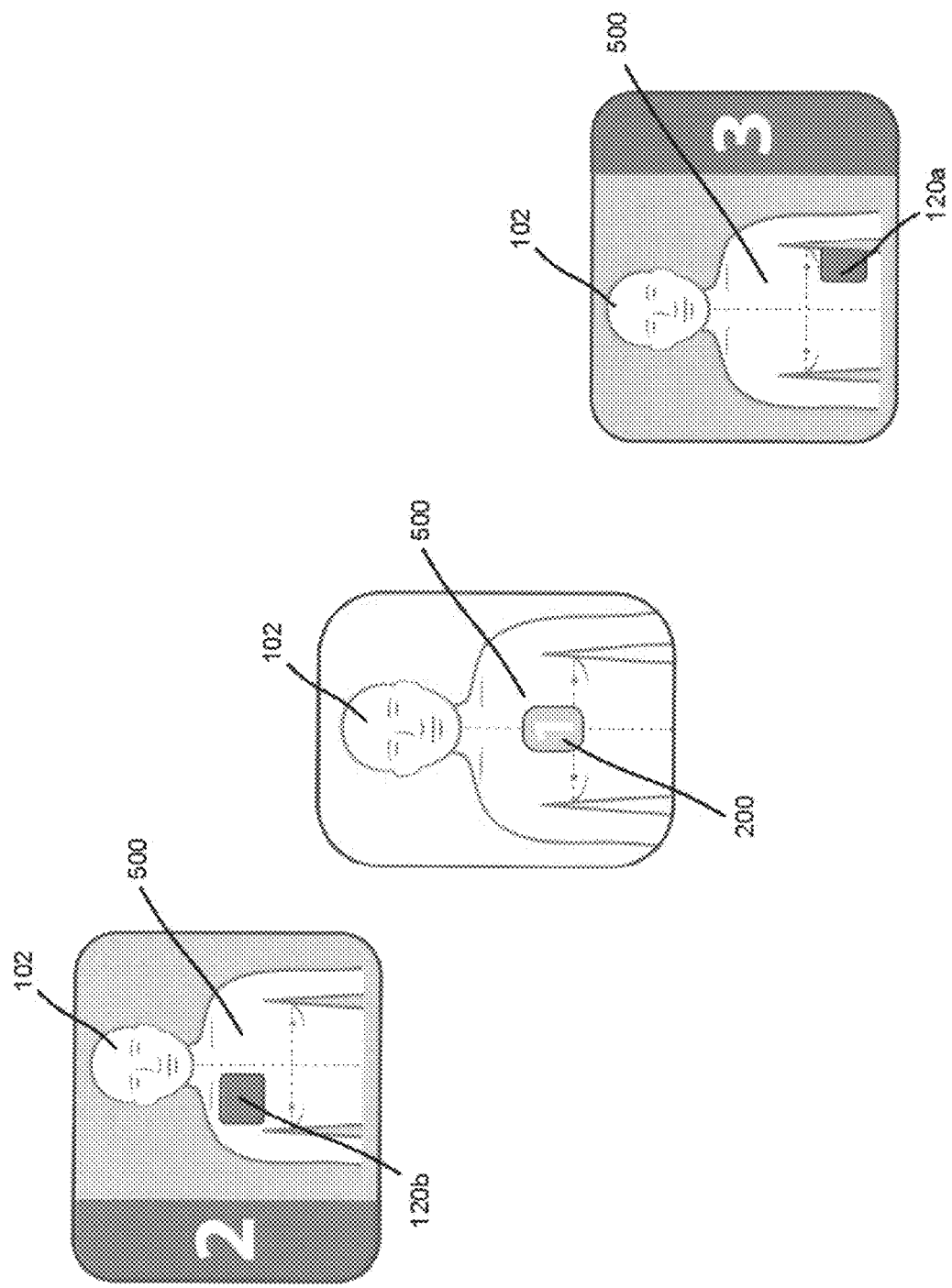
FIG. 5 is an illustration of the deployment of the self-contained response unit.

Referring to FIGS. 4 and 5, to deploy the response unit 200, the response unit 200 is removed from its packaging (400). For instance, a hermetic seal or gasket sealing the open sides of the compartment can be punctured, torn, or otherwise opened. The response unit 200 is positioned on the chest 500 of the victim 102 (402) with the bottom face 206 of the response unit in contact with the chest 500.

The electrode pads 120 can be removed from the compartment (404) and positioned on the chest 500 of the victim 102 (406). For instance, two electrode pads 120a, 120b may be provided in the response unit 200 for placement on the chest 500 according to an anterior-apex placement scheme in which an apex electrode 120a is applied to the lower left side of the victim 102 and a sternum electrode 120b is applied to the upper left chest of the victim 102. Other electrode placement schemes are also possible. In some examples, the electrode pads 120 can be removed prior to positioning the response unit 200 on the chest.

The response unit 200 is connected, e.g., via a cable connection, to an AED or other electronic device (408). Once the electrode pads 120 and the response unit 200 are positioned on the victim, the caregiver can deliver CPR (410) to the victim and/or defibrillate the victim (412) as needed.

In some examples, visual cues, such as numbers, illustrations, or instructions, are provided on the response unit to instruct the caregiver in the deployment of the response unit. Instructions may be provided on the top side 204 of the response unit. Instructions may be provided on individual components of the response unit, e.g., instructions for the deployment of the electrode pads may be provided on each electrode pad and instructions for the deployment of the sensors may be provided on the top side of the response unit.

It is to be understood that the foregoing description is intended to illustrate and not to limit the scope of the invention, which is defined by the scope of the appended claims. Other embodiments are within the scope of the following claims.

What is claimed is:

1. An apparatus comprising:
   a housing comprising at least two sides defining an interior space therebetween;
   a sensor coupled with one of the sides of the housing;
   an electrode pad removably disposed within the interior space defined by the sides of the housing; and
   an electrical interface in communication with one or more of the sensor or the electrode pad and configured to be connected to a defibrillation device external to the housing.

2. The apparatus of claim 1, comprising a dispenser disposed within the interior space defined by the sides of the housing.

3. The apparatus of claim 2, wherein the electrode pad is arranged on the dispenser.

4. The apparatus of claim 2, wherein the dispenser comprises a roller.

5. The apparatus of claim 4, wherein at least a portion of the electrode pad is rolled around the roller.

6. The apparatus of claim 2, wherein the dispenser is coated with a release agent.

7. The apparatus of claim 1, comprising two electrode pads removably disposed within the interior space defined by the sides of the housing.

8. The apparatus of claim 7, wherein each electrode pad is arranged on a corresponding dispenser disposed within the interior space defined by the sides of the housing.

9. The apparatus of claim 1, wherein the sensor comprises a motion detection device.

10. The apparatus of claim 1, comprising a cover surrounding the interior space defined by the sides of the housing.

11. A method comprising:
    providing a housing comprising at least two sides defining an interior space therebetween, wherein a sensor is coupled with one of the sides of the housing;
    removing an electrode pad from the interior space defined by the sides of the housing; and
    connecting one or more of the sensor or the electrode pad to a defibrillation device external to the housing.

12. The method of claim 11, wherein removing the electrode pad includes removing the electrode pad from a dispenser disposed within the interior space defined by the sides of the housing.

13. The method of claim 11, wherein removing the electrode pad includes removing the electrode pad from a roller disposed within the interior space defined by the sides of the housing.

14. The method of claim 13, wherein removing the electrode pad includes unrolling the electrode pad.

15. The method of claim 11, comprising opening a cover surrounding the interior space defined by the sides of the housing.

16. The method of claim 11, comprising positioning the housing on a chest of a victim of cardiac arrest.

17. The method of claim 11, comprising positioning the electrode pad on a chest of a victim of cardiac arrest.

* * * * *